United States Patent [19]

Cournoyer et al.

[11] 4,307,017
[45] Dec. 22, 1981

[54] XANTHENE COMPOUNDS

[75] Inventors: Richard L. Cournoyer, Dorchester; James W. Foley, Andover, both of Mass.

[73] Assignee: Polaroid Corporation, Cambridge, Mass.

[21] Appl. No.: 194,463

[22] Filed: Oct. 6, 1980

Related U.S. Application Data

[63] Continuation-in-part of Ser. No. 169,834, Jul. 17, 1980, which is a continuation-in-part of Ser. No. 106,901, Dec. 26, 1979, abandoned.

[51] Int. Cl.³ ............................................. C07D 513/10
[52] U.S. Cl. ................................. 260/239.95; 548/207
[58] Field of Search ..................... 260/239.95; 548/207

[56] References Cited

U.S. PATENT DOCUMENTS 4,231,929 11/1980 Bloom et al. ......................... 548/207

OTHER PUBLICATIONS

Müller, Methoden der Organischen Chemie, Georg. Thieme Verlag Stuttgart, 1970, p. 78.

Primary Examiner—Henry R. Jiles
Assistant Examiner—Bernard Dentz
Attorney, Agent, or Firm—Sybil A. Campbell

[57] ABSTRACT

The present invention is concerned with novel xanthene compounds of the formulae

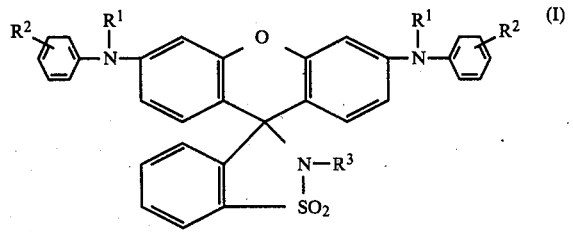

and

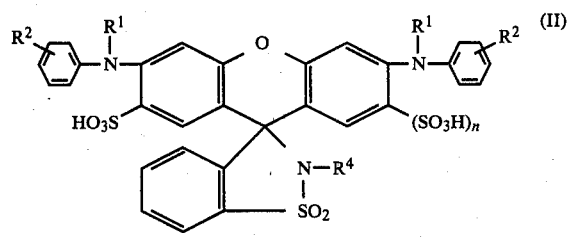

wherein each $R^1$ the same or different is alkyl or benzyl; each $R^2$ the same or different is an electron-withdrawing group having a positive sigma value greater than 0.6; $R^3$ is hydrogen or alkyl; $R^4$ is alkyl; and n is 0 or 1, said $R^2$ group being ortho, meta or para to said N atom. The subject compounds are useful as light-screening dyes in photographic products and processes.

12 Claims, No Drawings

XANTHENE COMPOUNDS

CROSS-REFERENCE TO RELATED APPLICATIONS

This application is a continuation-in-part of copending U.S. patent application Ser. No. 169,834, filed July 17, 1980, which, in turn, is a continuation-in-part of U.S. patent application Ser. No. 106,901 filed Dec. 26, 1979, now abandoned.

BACKGROUND OF THE INVENTION

1. Field of the Invention

This invention relates to novel xanthene compounds and to their use, e.g., as light-screening dyes in photographic products and processes.

2. Description of the Prior Art

It is well known that photographic film, and especially multicolor films, may and generally do vary from lot to lot, notwithstanding efforts to "repeat" previous films Manufacturers of multicolor photographic films have developed a number of procedures to minimize the effects upon the final multicolor image of unavoidable variations in the manufacturing operations. These variations are reflected primarily in shifts in color balance as reflected in mismatching of the D log E curves of the individual red, green and blue exposures. Equipment used to coat multicolor films is highly precise but variations between intended coverage of silver halide and/or the dye image-forming materials do occur. Repeat batches of silver halide emulsions may, and usually do, vary in their photographic response. Individual layers may be dried to slightly different degrees. Films are stored for a period of time after coating to allow the films to "age", so that changes in sensitometry following coating have an opportunity to reach a plateau prior to sale. If the film is designed to be developed by a photofinisher or in a darkroom, processing of the exposed multicolor film is controlled within very narrow limits, typically within plus or minus a half degree of a prescribed temperature, in order to minimize sensitometric variations from film to film. Where the multicolor film is of the negative type, an opportunity to adjust the sensitometry occurs in printing the desired final positive image, during which operation the printing exposure may be appropriately color filtered.

The basic sources of sensitometric variations noted above exist also in multicolor diffusion transfer films, with the added complication that once the film is shipped, the sensitometric properties are essentially fixed. The opportunity for adjustment provided in darkroom processing, practically speaking, is unavailable for users of self-developing films. While professional and advanced amateur photographers may be skillful enough to utilize color correction filters to at least partially "rebalance" the color balance, ordinary users of the film would only be confused by such additional operations.

It is well known to use light-screening dyes in photographic elements. Such a dye may be incorporated as a filter dye in a light-sensitive emulsion layer(s) or in a layer coated over one or more light-sensitive emulsion layers or between two differently color-sensitized emulsion layers to modify the light record in the emulsion layer or to control the spectral composition of light falling on the underlying light-sensitive layer, or it may be incorporated as an anti-halation dye in a non-light-sensitive layer positioned on either side of a support carrying the light-sensitive layer(s).

The dyes employed for these purposes, in addition to having the requisite spectral absorption characteristics for their intended use, should be photochemically inert, that is, they should not have any adverse effect on the properties of the light-sensitive emulsion layer(s), and also, they should be capable of being decolorized or removed during photographic processing so as not to leave stain in the processed photographic element. In photographic processes where the dye is removed by being dissolved in a processing solution, it is usually preferred that the dye also decolorize in order to avoid contamination of the processing solution and to prevent staining from residual dye in the processed light-sensitive element.

Though various classes of dyes have been proposed for use in antihalation and color correction filter layers, the dyes heretofore employed have not been altogether satisfactory. Some of the dyes tend to reduce sensitivity fog or exert or other adverse effect on the light-sensitive material. However, the major drawback of previously employed dyes is their tendency to cause stain due to incomplete decolorization or reversal of some of the decolorized form to the original colored form. For example, some classes of dyes rely on the presence of a reagent, such as, a sulfite for "bleaching", i.e., decolorization and unless the dyes are removed from the light-sensitive material during or after processing, their color may reappear in time.

Among the classes of light-screening dyes used previously are the triarylmethanes and xanthenes. For example, U.S. Pat. Nos. 1,879,537; 1,994,876; 2,350,090 and 3,005,711 disclose the use of fuchsone-type dyes in antihalation layers, and U.S. Pat. Nos. 3,406,069 and 3,615,548 are concerned with the metal chelates of fuchsone dyes as antihalation dyes. These and other types of triarylmethane dyes suffer from one or more of the drawbacks discussed above, and in particular, prior dyes of this type have been difficult to keep decolorized at the pH's normally encountered during processing subsequent to "bleaching" and in the final product. Xanthenes have been employed in antihalation layers that are removed during photographic processing. For example, U.S. Pat. Nos. 2,182,794; 2,203,767 and 2,203,768 disclose the use of rhodamine dyes in certain antihalation layers that are removed during processing in an acid bath or a plain water rinse bath depending upon the solubility characteristics of the particular layer.

Aforementioned U.S. patent application Ser. No. 169,834 is directed to photographic products and processes employing light-screening dyes of the formulae

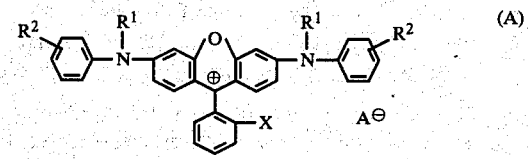

(A)

and

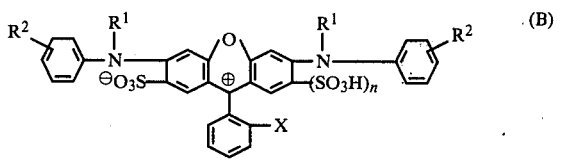 (B)

wherein each $R^1$ the same or different is alkyl, each $R^2$ the same or different is an electron-withdrawing group having a positive sigma value greater than 0.6, X is

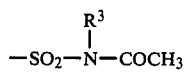

or

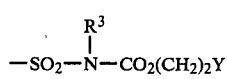

wherein $R^3$ is alkyl and Y is an electron-withdrawing group, n is 0 or 1 and A is an anion, said $R^2$ group being ortho, meta or para to said N atom. These compounds are colored, i.e., capable of absorbing visible radiation, and at an alkaline pH, are converted to a colorless product by undergoing an irreversible cleavage reaction with base. The colorless product formed is a new compound which is different from and non-reversible to the colored compound by a change in pH. In particular, it is the X group substituted on the phenyl moiety that undergoes the irreversible cleavage reaction in alkaline solution that is complete within a predetermined time at a predetermined alkaline pH to give the new colorless compound, namely, the cyclic sulfonamide,

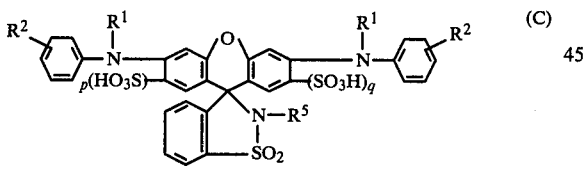 (C)

wherein p is 0 or 1; q is 0 when p is 0 and is 0 or 1 when p is 1; $R^5$ is alkyl and $R^1$ and $R^2$ have the same meaning given above. These compounds offer advantages over the light-screening dyes previously used because of their ability to decolorize completely and irreversibly to a substantially inert colorless product.

Besides being the product of the cleavage reaction, certain of the compounds of formula C and similar compounds wherein the N atom of the cyclic sulfonamido ring is unsubstituted are useful as intermediates in the synthesis of the compounds of formulae A and B. For example, as discussed in said application, the compounds of formulae A and B may be prepared in a known manner (a) by reacting a compound of the formula

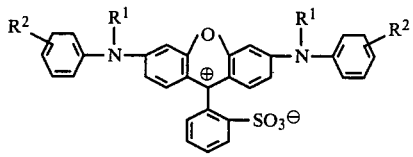

wherein each $R^1$ the same or different is alkyl and each $R^2$ the same or different is an electron-withdrawing group having a positive sigma value greater than 0.6 with phosphorus pentachloride or thionyl chloride to give the corresponding sulfonyl chloride of the formula

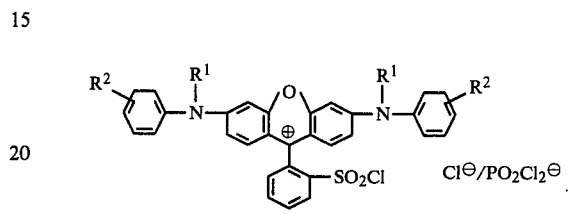

wherein $R^1$ and $R^2$ have the same meaning given above;

(b) reacting said sulfonyl chloride with ammonia to give the corresponding cyclic sulfonamide of the formula

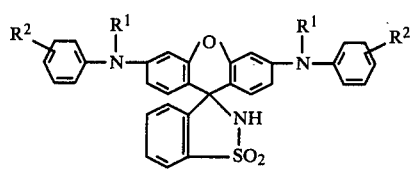

wherein $R^1$ and $R^2$ have the same meaning given above;

(c) reacting said cyclic sulfonamide with an alkylating agent to give the corresponding N–$R^3$ sulfonamide of the formula

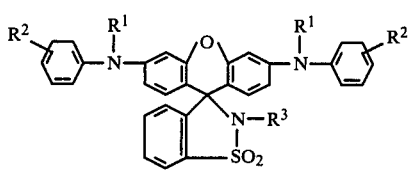

wherein $R^3$ is alkyl and $R^1$ and $R^2$ have the same meaning given above;

(d) reacting said N—$R^3$ sulfonamide with a reducing agent to give the corresponding reduction product of the formula

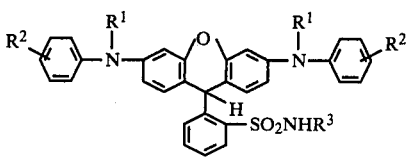

wherein $R^1$, $R^2$ and $R^3$ have the same meaning given above;

(e) reacting said reduction product with the appropriate acylating agent, for example, $CLCOCH_3$ or $ClCO_2(CH_2)_2Y$ to give the leuco dye precursor of the formula

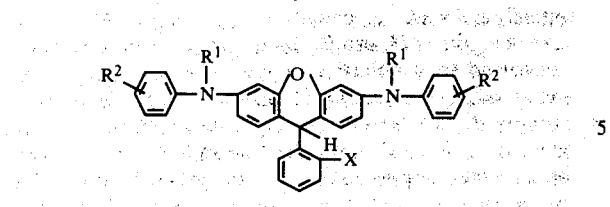

wherein X is

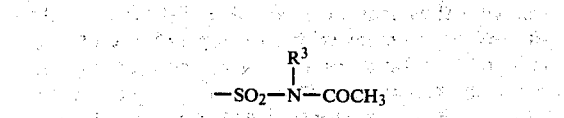

or

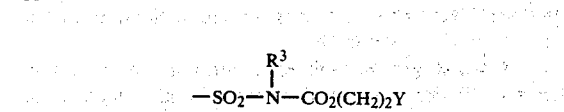

wherein Y is an electron-withdrawing group and $R^1$, $R^2$ and $R^3$ have the same meaning given above; and (f) oxidizing said leuco dye precursor preferably using o-chloranil as the oxidizing agent followed by isolating the dye product from its o-chloranil complex with an acid to yield the dye product.

To synthesize the sulfo-substituted xanthene compounds, the leuco dye precursor of step (e) is reacted with chlorosulfonic acid in a solvent, such as, methylene chloride to give mainly the monosulfonated product or in a more polar solvent, such as, acetic anhydride to give essentially the disulfonated product of the formulae

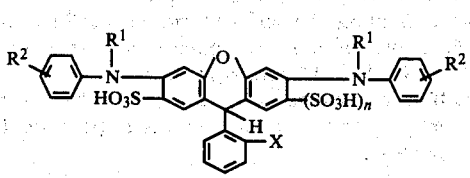

wherein $R^1$, $R^2$ and X have the same meaning given above and n is 0 or 1. This sulfonated leuco dye precursor is then oxidized in the same manner as described in step (f) above.

The starting materials for use in step (a) may be prepared, for example, (1) by reacting sulfonefluorescein dichloride with a substituted aniline,

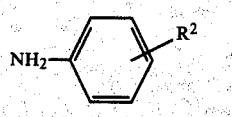

wherein $R^2$ is an electron-withdrawing group having a positive sigma value greater than 0.6 to give the mono-substituted sulfonefluorescein compound of the formula

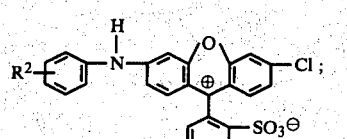

(2) reacting the mono-substituted compound of step (1) with a substituted aniline,

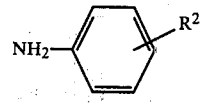

wherein $R^2$ is an electron-withdrawing group having a positive sigma value greater than 0.6 to replace the other chloro group and give the compound of the formula

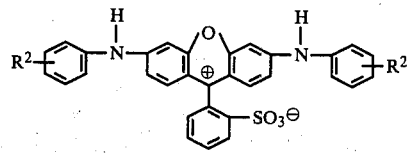

wherein said $R^2$ groups may be the same or different; and (3) reacting the compound of step (2) with an alkylating agent to substitute one of said N atoms with an alkyl group and then reacting the compound thus obtained with a second alkylating agent to substitute the other said N atom with a different alkyl group or reacting the compound of step (2) with an alkylating agent to substitute both of said N atoms with alkyl groups, the same. Where the $R^2$ substituent(s) of the N,N-dialkylated compound are alkylthio, the compound of step (3) is then converted to the corresponding alkylsulfonyl-substituted compound before converting to the sulfonyl chloride.

Where said $R^2$ groups are the same, both chloro groups of the sulfonefluorescein dichloride starting material may be replaced in a single step, but preferably, they are replaced in a stepwise fashion as shown above.

The present invention is directed to certain xanthene compounds disclosed in said application Ser. No. 169,843, for example, the compounds produced in steps (b) and (c) above. These compounds are not only useful as intermediates in the synthesis of certain light-screening dyes but these and certain other compounds disclosed therein also have been found useful as light-screening dyes per se.

SUMMARY OF THE INVENTION

It is therefore the primary object of the present invention to provide certain xanthene compounds.

It is another object of the present invention to provide xanthene compounds useful in photographic products and processes.

Other objects of this invention will in part be obvious and will in part appear hereinafter.

This invention accordingly comprises the products and compositions processing the features, properties and the relation of elements which are exemplified in the following detailed disclosure and the scope of the application of which will be indicated in the claims.

For a fuller understanding of the nature and objects of the present invention, reference should be had to the following detailed description.

DETAILED DESCRIPTION OF THE INVENTION

The compounds provided by the present invention may be represented by the formulae

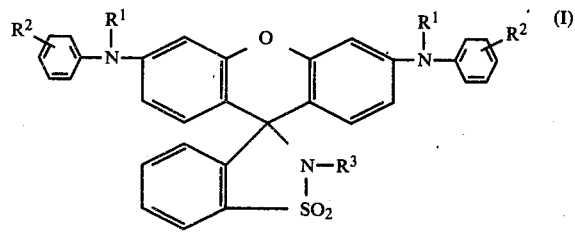

and

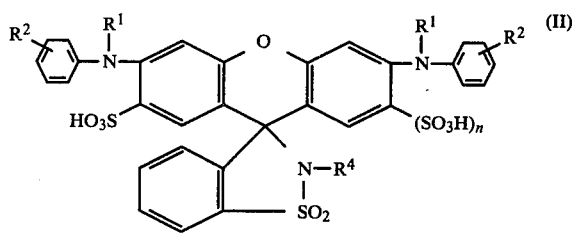

wherein each $R^1$ the same or different is alkyl or benzyl; each $R^2$ the same or different is an electron-withdrawing group having a positive sigma value greater than 0.6; $R^3$ is hydrogen or alkyl; $R^4$ is alkyl; and n is 0 or 1, said $R^2$ group being ortho, meta or para to said N atom. Typically said $R^1$ groups are alkyl containing 1 to 7 carbon atoms, e.g., methyl, ethyl, n-propyl, n-butyl, s-butyl, n-hexyl and benzyl, and said $R^3$ and $R^4$ groups are alkyl containing 1 to 4 carbon atoms. Usually the $R^1$ groups are the same, and the $R^2$ groups are the same.

Preferred electron-withdrawing groups having a positive sigma value ($\sigma^-$) greater than 0.6 include nitro; cyano; $-SO_2CH_3$; $COCH_3$; $-SO_2N(CH_2Ph)_2$; and $-SO_2N(CH_3)_2$. The sigma value for these and other groups, such as, $-CHO$, $-COOH$, $-COOC_2H_5$ and $-CONH_2$ have been reported by Eugen Müller, Methoden Der Organischen Chemie, Georg Thieme Verlag, Stuttgart, 1970, p. 78 in terms of $\sigma^-$ values based on the ionization of p-substituted phenols.

The subject xanthene compounds, though also useful as photographic light-screening dyes, do not undergo an irreversible cleavage reaction but decolorize in response to a change in pH. These pH-sensitive dyes are initially colored, i.e., capable of absorbing visible radiation at a given pH, usually about pH 6 or below and are converted to a colorless or non-light-absorbing form above said pH. Because of their ability to decolorize completely in base without requiring an additional reagent, such as, a sulfite for the "bleaching" reaction and because they remain colorless in aqueous solution above said given pH to pH 14, compounds may be selected for use in a given photographic process on the basis of final pH so that they may be retained in the photographic light-sensitive element without the possibility of color reappearing in time. Besides being non-staining, the compounds usually are substantially inert with respect to the light-sensitive material and thus, may be positioned, for example, in a layer adjacent to a silver halide emulsion layer without having any adverse effect on the properties of the emulsion.

As noted above, the subject compounds may be synthesized in the manner described in aforementioned application Ser. No. 169,834 by reacting the selected 3,6-dianilino-substituted xanthene starting material with phosphorus pentachloride or thionyl chloride to give the corresponding sulfonyl chloride followed by treating with ammonia to produce the cyclic sulfonamide. Where the $R^3$ group is alkyl, the cyclic sulfonamide is reacted with the selected alkylating agent to give the corresponding N-alkylated sulfonamide. The sulfo-substituted compounds may be prepared by reducing the N-alkylated sulfonamide, reacting with chlorosulfonic acid in a solvent, such as, methylene chloride to give mainly mono-sulfonated compound or in a more polar solvent, such as, acetic anhydride to give essentially disulfonated compound and then oxidizing to the product. Alternatively, the sulfonated products may be prepared by treating the sulfo-substituted xanthene light-screening dyes of aforementioned U.S. patent application Ser. No. 169,834 with aqueous alkali.

The following examples are given to further illustrate the present invention and are not intended to limit the scope thereof.

EXAMPLE 1

Preparation of the compound having the formula

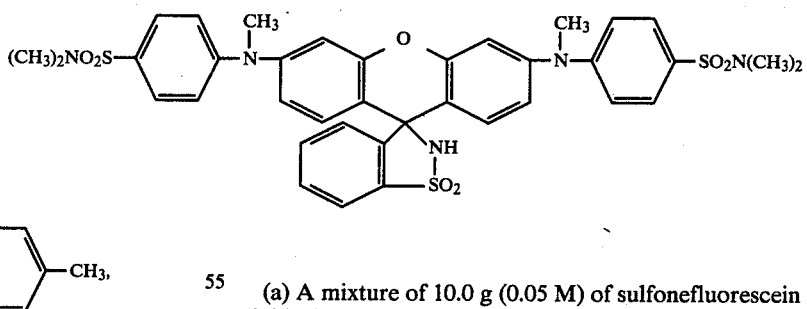

(a) A mixture of 10.0 g (0.05 M) of sulfonefluorescein dichloride

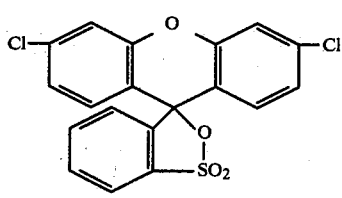

and 20.26 (0.05 M) of p-(N,N-dimethylsulfonamido)aniline in 160 ml of 2-methoxyethyl ether were stirred together for 24 hours, filtered, washed with a small amount of 2-methoxyethyl ether, then with ether and dried in vacuo to give 18.53 g of the compound

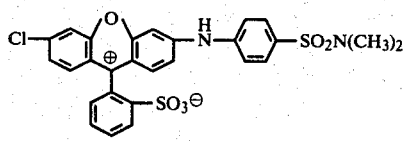

(b) The above compound, 20.0 g (35.1 mM) and 14.1 g (70.3 mM) of p-(N,N-dimethylsulfonamido)aniline and 20 ml 1-methyl-2-pyrrolidinone were heated in an oil bath at 170° C. under an atmosphere of nitrogen for 4 hours. The deep magenta mixture was then treated with 100 ml 1-methyl-2-pyrrolidinone, cooled to room temperature and poured into a solution of 200 ml conc. HCl and 1400 ml water. This mixture was centrifuged, and the residue was washed with saturated sodium chloride solution and placed in a crystallizing dish to air dry over the weekend. The residue, which contained a considerable amount of sodium chloride, was then dried under vacuum at (70° C.) for 4 hours to give 25.4 g of crude material comprising the compound

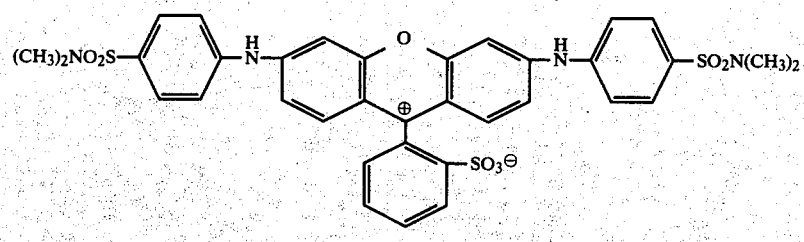

(c) The compound prepared in step (b), 25.4 g, (34.7 mM) was dissolved in 300 ml dry dimethylsulfoxide. (Some solid material was observed floating in the solution which was probably sodium chloride.) A 50% sodium hydride dispersion, 6.72 g, was added to the above solution all at once and then allowed to stir at room temperature for 1½ hours. The green solution was cooled in an ice bath and iodomethane (300 g) was added dropwise over a period of about one hour. The mixture was allowed to warm to room temperature overnight with stirring. The mixture was poured into three liters of water containing 200 ml conc. HCl and extracted with methylene chloride (6×200 ml). The combined methylene chloride extracts were washed with a 2 N HCl solution (5×1000 ml) and dried over sodium sulfate. The solvent was removed in vacuo to give 10.41 g of the compound

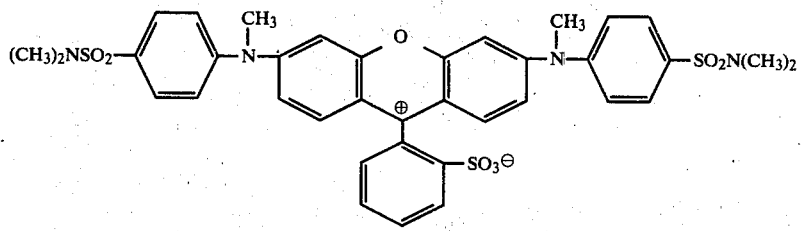

(d) The compound prepared in step (c), 10.4 g (about 13.7 mM), was dissolved in 150 ml of chloroform and treated with 6.25 g (30 mM) of phosphorus pentachloride. The resulting mixture was heated at reflux for 5 hours and then allowed to stir at room temperature overnight. The purple solution was transferred to a separatory funnel, washed with water (2×75 ml) and then dried over magnesium sulfate. The mixture was filtered to remove the magnesium sulfate and the filtrate cooled in an ice bath. The filtrate comprised the sulfonyl chloride of the formula

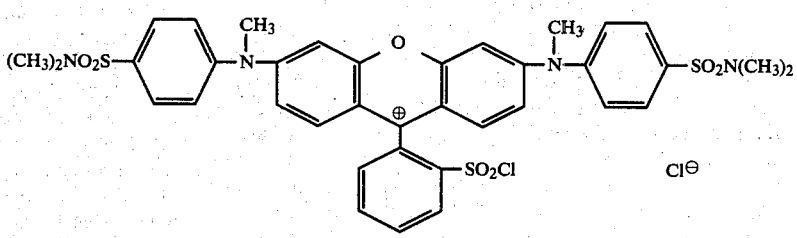

(e) Ammonia gas was bubbled into the filtrate obtained in step (d) until saturated. It was then allowed to come to room temperature and stirred overnight. (The purple color of the solution became much less intense.) The mixture was filtered to remove the salts, and the solvent removed from the filtrate in vacuo leaving 10.67 g of residue. The residue was taken up in 25 ml chloroform:methanol (100:1), applied to medium pressure liquid chromatography column and eluted with 1000 ml chloroform:methanol (100:1), then with dichloroform:methanol (50:1). Fractions 2 to 7 were combined and the separation repeated eluting with chloroform:methanol (100:1) to give 5.0 g (90–95% purity) of the title compound.

EXAMPLE 2

Preparation of the compound of the formula

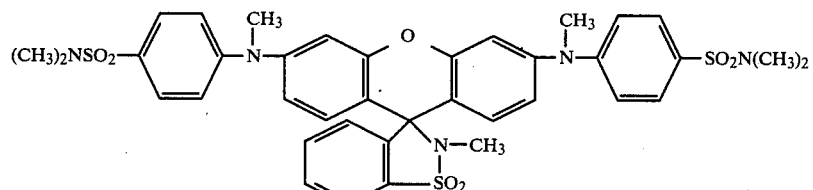

The compound prepared in Example 1, 4.85 g (6.4 mM) was dissolved in 60 ml of dry 2-methoxyethyl ether. To this solution, 0.88 g (7.9 mM) of potassium-t-butoxide was added all at once and the resulting solution allowed to stir at room temperature for one hour. The dark mixture was cooled in an ice bath and 0.75 ml (1.0 g; 7.9 mM) of dimethylsulfate was added all at once. The mixture was allowed to come to room temperature overnight and then was poured into 600 ml of water containing 30 g of sodium chloride. The mixture was stirred for about 15 minutes, filtered and the product washed with water. The product was taken up in about 100 ml of methylene chloride, washed with saturated sodium chloride solution (2×75 ml) and dried over sodium sulfate. Methylation did not go to completion so the methylation was repeated on the dried material which was dissolved in 60 ml dry 2-methoxyethyl ether and then treated with 0.95 g (8.47 mM) of potassium-t-butoxide. This mixture was heated for one hour at 50°, then cooled in an ice bath. The mixture was then treated with 0.80 ml (1.068 g; 8.47 mM) of dimethyl sulfate. The resulting reaction mixture was allowed to come to room temperature and stirred for 5 days. The mixture was poured into 600 ml water containing 30 g of sodium chloride and allowed to stir for 15 minutes. The reaction product was filtered, washed with water and dissolved in approximately 100 ml of methylene chloride. The methylene chloride solution was washed with saturated sodium chloride solution and then dried over sodium sulfate. The solvent was removed to give 3.7 g of the title compound.

EXAMPLE 3

Preparation of the compound having the formula

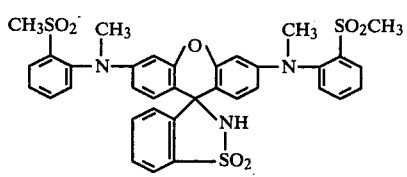

(a) A mixture of 68.9 g (0.17 M) of sulfonefluorescein dichloride, 50 g (0.36 M) 2-methylthioaniline and 7.26 g (0.18 M) magnesium oxide in 135 ml of dimethyl sulfoxide was heated at 140°–145° C. under nitrogen with stirring for 2.5 hours and then poured into 1500 ml of 2 N hydrochloric acid with vigorous stirring. The mixture was stirred for about one hour, the crude reaction product filtered, washed voluminously with water and dried in vacuo overnight to give 94.9 g of solid comprising the compound of the formula

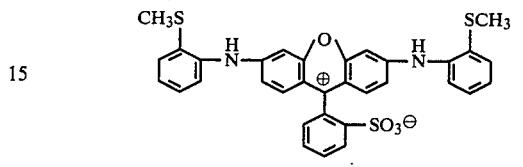

(b) To a mixture of 50 g (0.082 M) of the compound prepared in step (a) in 500 ml of dimethyl sulfoxide under at atmosphere of nitrogen was added 19.65 g of 50% sodium hydride (previously washed with hexane; ≡9.82 g, 0.41 M). The resulting mixture was allowed to stir at room temperature for two hours, and then 100 g (0.70 M) of iodomethane was added dropwise to the green solution. The mixture turned magenta in color within minutes. The mixture was allowed to stir at room temperature over the weekend, then poured into 6000 ml 2 N hydrochloric acid, stirred for approximately one-half hour and filtered. The filter cake was treated with approximately 1200 ml of methylene chloride, washed with 1 N hydrochloric acid (4×500 ml), ½-saturated sodium chloride solution (1×500 ml) and then dried over magnesium sulfate. The solvent was evaporated under reduced pressure leaving 57.67 g of crude reaction product. High pressure liquid chromatography of the crude product gave 20.47 g of the compound having the formula

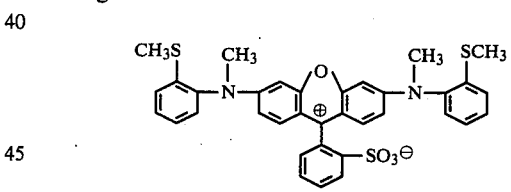

Overall yield from sulfonefluorescein was 35% by weight.

A 1.0 g sample was dissolved in a minimum amount of methylene chloride, precipitated in about 100 ml of ether, and the precipitate filtered and dried in vacuo. (Ethanol: λmax 543 nm—Epsilon 98,000).

(c) A solution of 10.0 g (15.7 mM) of the compound of step (b) in 75 ml methylene chloride was added dropwise to a solution of 20.2 g of 80–90% m-chloroperoxybenzoic acid (equivalent to 16.2–18.2 g) in 400 ml methylene chloride. The temperature increased from 18° to 32° C. The mixture was allowed to stir at room temperature overnight. The mixture was then filtered to remove a small amount of m-chlorobenzoic acid. The filtrate was washed with 10% aqueous sodium hydrogen sulfite (3×250 ml), 5% aqueous sodium bicarbonate (3×250 ml), ½-saturated sodium chloride solution (2×250 ml) and dried over magnesium sulfate. The solvent was evaporated under reduced pressure, and the residue dried under high vacuum for about one hour to give 9.7 g of the compound of the formula

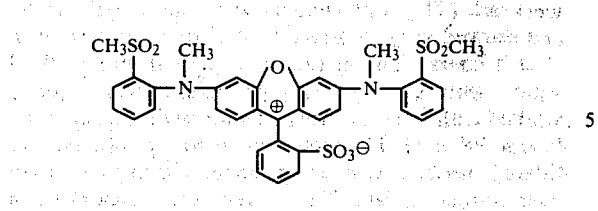

(Ethanol: λmax 534 nm—Epsilon 105,000).

(d) To a solution of 17.89 g (24.45 mM) of the compound of step (c) dissolved in 400 ml of chloroform was added 10.6 g (50.9 mM) of phosphorus pentachloride. The resulting mixture was heated at reflux for 6 hours, then allowed to come to room temperature overnight. The reaction product comprising the compound of the formula

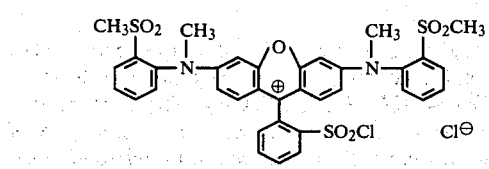

was used directly in the next step without isolation from the reaction mixture.

(e) The reaction mixture of step (d) was cooled to about 5° C. in an ice-bath. Then anhydrous NH₃ gas was bubbled into the mixture until it was saturated. The temperature rose from 5° to 22° C. The ice-bath was removed and the reaction mixture allowed to warm to room temperature. After 6 hours of stirring, the mixture was filtered to remove the salts. The filtrate was washed with water containing a little sodium chloride (3×200 ml) and then dried over anhydrous sodium sulfate. The solvent was evaporated under reduced pressure to give 18.58 g of crude product, which was further purified by high pressure liquid chromatography to yield 15.27 g of the title compound as a light pink solid.

EXAMPLE 4

Preparation of the compound having the formula

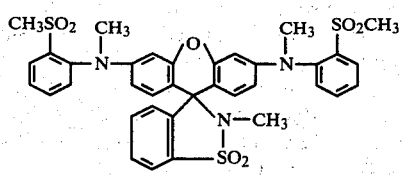

To a mixture of 0.50 g (0.71 mM) of the compound of Example 3 in 10 ml methylene chloride and 0.75 ml of 1.0 N sodium hydroxide (0.75 mM) in 10 ml water was added 232 mg (≡197.3 mg; 0.71 mM) of 85% tetra-n-butylammonium chloride and 0.25 ml (≡568; 4.0 mM) of iodomethane. After about 45 minutes the reaction appeared to be essentially complete. (TLC showed no starting material.) The reaction was allowed to stir overnight, and the TLC looked the same. The methylene chloride layer was separated and washed with water (5×25 ml), dried over sodium sulfate and the solvent evaporated leaving 0.57 g of the reaction product which was crystallized from about 5 ml of ethanol to give the title compound.

EXAMPLE 5

Preparation of the compound having the formula

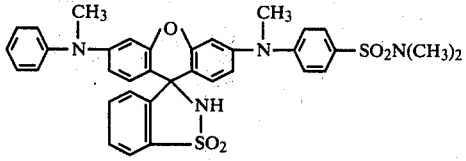

The title compound was prepared according to the procedure described in Example 1 above except that step (b) was carried out as follows.

One gram (1.76 mM) of the compound having the formula

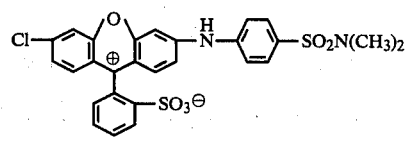

in 4 ml dry 1-methyl-2-pyrrolidinone and 0.345 ml (0.350 g; 3.75 mM) of aniline were heated together in an oil bath at 150° C. for 30 minutes. TLC with chlorofom/methanol (9:1) indicated a single magenta spot with no starting material present. The mixture was stirred with 40 ml water, filtered, washed with water and dried in vacuo overnight to give 1.09 g of the compound having the formula

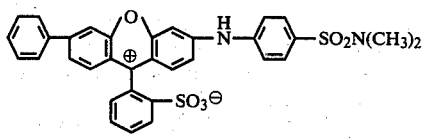

EXAMPLE 6

Preparation of the compound having the formula

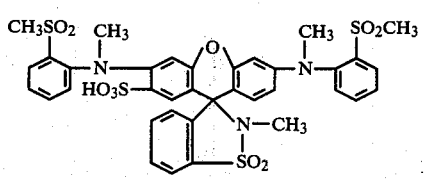

The compound having the formula

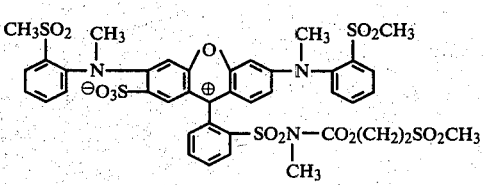

was treated with aqueous 1 N NaOH to give the title compound.

EXAMPLE 7

Preparation of the compound having the formula

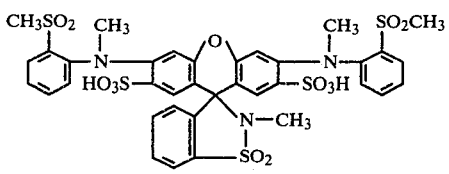

The compound having the formula

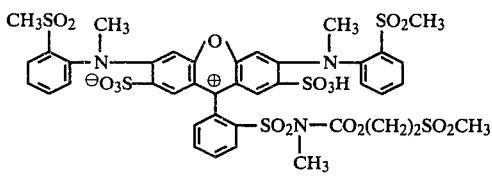

was treated with aqueous 1 N NaOH to give the title compound.

Sulfonefluorescein dischloride was prepared as follows:

In a 5 liter 3-necked round-bottom flask equipped with a paddle stirrer, a reflux condenser and a thermometer was placed 1.5 liters of ethyl acetate which was then cooled to 0° C. using an ice bath. Sulfonefluorescein (250 g) was added followed by 200 ml of thionyl chloride. The temperature rose slightly. The temperature was allowed to fall back to 0° C. 750 ml of N,N-dimethylformamide (DMF) was then added all at once. The temperature rose to about 30° C. After the additions were completed, the mixture was stirred for 1 hour. The ice bath was removed to allow the temperature of the reaction mixture to rise to room temperature after which the mixture was placed on a steam bath and heated to reflux with stirring. During heating the mixture became lighter in color and thicker. (The color was brown.) After refluxing 10 to 15 minutes the reaction mixture was placed in an ice bath and cooled to 0° C. with stirring continuing. The cold reaction mixture was filtered and washed with cooled 15% DMF/ethyl acetate solution until the color of the precipitate became as light as possible, then washed with ether. After sucking under a rubber dam, the sulfonefluorescein dichloride was air dried. Yield 184.3 g (68%); 99.7% pure by L. C.

The monosulfonated and disulfonated compound of the following formulae were prepared as described below.

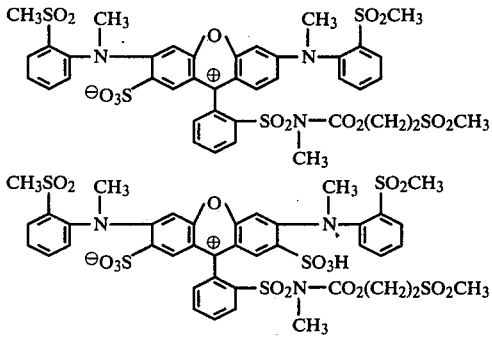

(1) A solution of 11.71 g (16.35 mM) of the compound of Example 4 in 150 ml glacial acetic acid was treated with 3.2 g (49 mg-atoms) of zinc dust under an atmosphere of nitrogen in a water bath at approximately 50° C. for about 8 hours, then at room temperature over the weekend. (TLC's of aliquots were taken periodically and showed varying amounts of starting material even after 8 hours.) The mixture was poured into 1500 ml water with stirring. The precipitate was filtered, washed with water and treated with methylene chloride (about 300 mls). The methylene chloride solution was filtered, washed with water (about 100 ml) and dried over sodium sulfate. The solvent was evaporated in vacuo yield 11.35 g (97%) of the compound of the formula

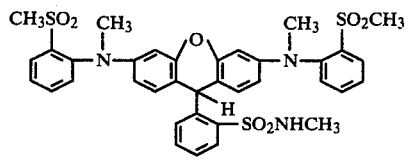

(2) A mixture of 10.4 g (14.5 mM) of the compound of step (1) in 125 ml dry pyridine was treated with 10.8 g (58 mM) of ClCO₂(CH₂)₂SO₂CH₃. The mixture was stirred at room temperature under an atmosphere of nitrogen overnight. (TLC of an aliquot showed no starting material, only a single spot corresponding to the leuco dye.) The mixture was poured into 1400 ml water and the precipitated reaction product filtered, washed with water and dried in vacuo to give 10.74 g of the compound of the formula

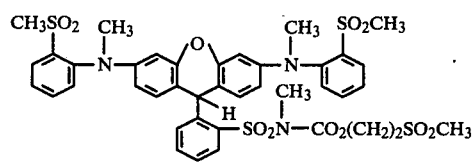

as a light pink solid.

(3) A solution of 500 mg (0.57 mM) of the compound of step (2) dissolved in 10 ml dry methylene chloride was treated with a solution of 0.084 ml of chlorosulfonic acid (≡147 mg; 1.2 mM) in 5 ml methylene chloride. A precipitate formed immediately. This mixture was allowed to stir at room temperature overnight. The methylene chloride was decanted and the residue was washed with methylene chloride. TLC showed the presence of a considerable amount of starting material.

The residue (0.567 g; 0.598 mM) was dissolved in approximately 10 ml methanol, treated with 294 mg (1.2 mM) of o-chloranil and heated at reflux for 30 minutes, then at room temperature for 2 hours. The precipitate was filtered, and the filtrate evaporated under reduced pressure (about 200 mg). The filtrate was treated using preparative TLC techniques to give 96 mg of single spot material corresponding to the monosulfonated product (soluble in chloroform; slightly soluble in methanol; insoluble in water).

(3a) A solution of 500 mg (0.57 mM) of the compound of step (2) dissolved in 5 ml acetic anhydride was treated with 0.084 ml (≡147 mg; 1.2 mM) of chlorosulfonic acid dropwise under an atmosphere of nitrogen. No precipitate had formed after 4 hours. The mixture was allowed to stir at room temperature overnight. Then the mixture was poured into 5 ml ether. The precipitate was filtered, washed with ether and dried in vacuo to give 0.56 g of solid. TLC of this solid showed the disulfonated product to be the major product.

Methanolic solutions of the compounds prepared in Examples 1 to 5 were added to a series of buffered solutions having a pH of 4, 5, 6 and 7, respectively, in order to determine the approximate pH at which these compounds become colored as the pH drops below alkaline values. As a comparison, the following compound disclosed in Beilstein's Handbuch der Organischen Chemie, Vol. 27, p. 544, also was added as a methanolic solution to a series of buffers.

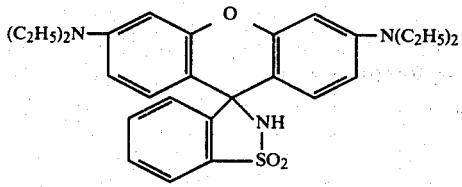

Compound X

The results are set forth in the Table below.

TABLE

| Compound | pH 4 | pH 5 | pH 6 | pH 7 |
|---|---|---|---|---|
| Ex 1 | ++ | o | o | o |
| Ex 2 | + | o | o | o |
| Ex 3 | + | + | o | o |
| Ex 4 | + | o | o | o |
| Ex 5 | ++ | + | + | o |
| Cpd X | +++ | +++ | ++ | + |

+++ = very intense color
++ = intense color
+ = faint color
o = no color

As discussed previously, the subject light-screening compounds are pH-sensitive dyes that are in their colored form at pH 6 or below and as evident from the results shown above, they are converted to their colorless form when contacted with aqueous base. In their colored form, the sulfamphthalein ring is open, for example,

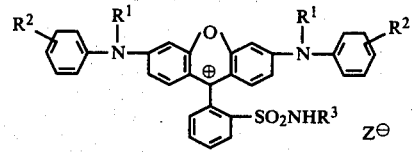

wherein $R^1$, $R^2$ and $R^3$ have the same meaning given above and Z is an anion, and in their colorless form, the sulfamphthalein ring is closed.

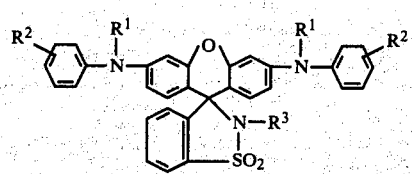

It will be appreciated that the sulfo-substituted compounds decolorize in a like manner.

Depending upon the particular photographic process, dyes may be selected from the subject compounds that remain colorless at the pH's normally encountered during processing subsequent to being converted to their colorless form so that they may be retained in a photographic film unit, e.g., a photosensitive element without the possibility of color reappearing in time. Typically, dyes may be selected for use as antihalation dyes, e.g., in a non-light-sensitive layer positioned intermediate a photosensitive silver halide emulsion layer and the support. Also, dyes may be selected for use as color correction filter dyes where absorption of light within a particular wavelength range during exposure is desirable for achieving appropriate color balance.

Whether used for antihalation, color correction or other photographic light-screening applications, the subject compounds, of course, should be in their colored or light-absorbing form initially, and thus, they should be incorporated in a layer having sufficient acidity to render the compounds colored. Useful layers include polymers which contain acid groups, e.g., carboxylic acid and sulfonic acid groups and polymeric acid or other polymeric layers containing polymeric or monomeric organic acids added in the amount necessary to give the level of acidity required for converting the selected dye compound to its colored form. The amount of additional acid needed, if any, may be readily determined empirically.

The use of the subject compounds as photographic light-screening dyes is disclosed and claimed in copending U.S. patent application Ser. No. 194,468 of Richard L. Cournoyer and James W. Foley filed concurrently herewith. For convenience, the specification of said application is specifically incorporated herein.

Since certain changes may be made in the hereinafter defined subject matter without departing from the scope of the invention herein involved, it is intended that all matter contained in the above description and examples be interpreted as illustrative and not in a limiting sense.

We claim:

1. A compound of the formula

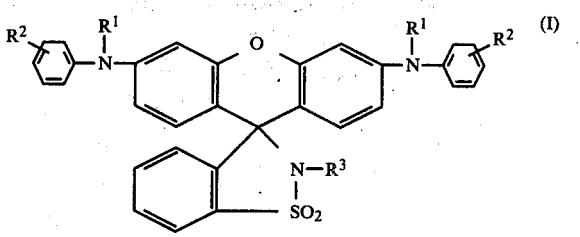

and

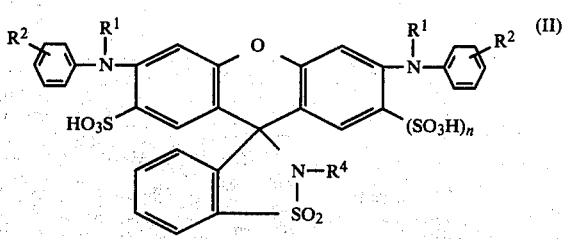

wherein each $R^1$ the same or different is alkyl containing 1 to 7 carbon atoms or benzyl, each $R^2$ the same or different is an electron-withdrawing group having a positive sigma value greater than 0.6; $R^3$ is hydrogen or alkyl containing 1 to 4 carbon atoms; $R^4$ is alkyl containing 1 to 4 carbon atoms; and n is 0 or 1, said $R^2$ group being ortho, meta or para to said N atom.

2. A compound as defined in claim 1 wherein each $R^1$ are the same.

3. A compound as defined in claim 1 wherein each $R^2$ are the same.
4. A compound as defined in claim 1 wherein $R^3$ is hydrogen.
5. A compound as defined in claim 1 wherein $R^3$ is alkyl.
6. A compound as defined in claim 1 wherein n is 0.
7. A compound as defined in claim 1 wherein n is 1.
8. The compound
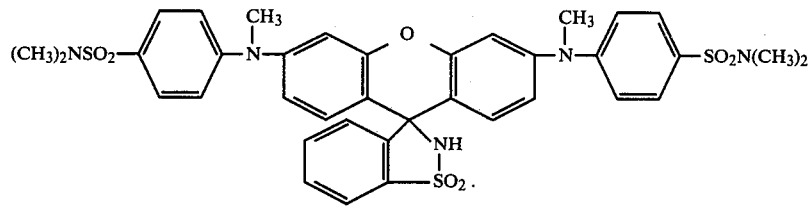
9. The compound
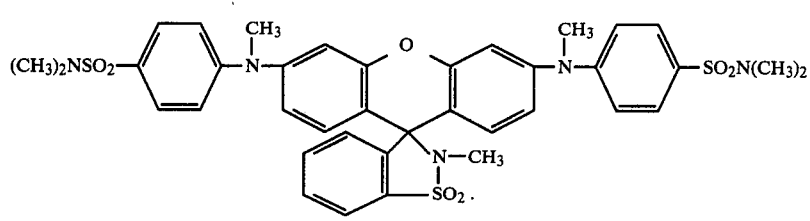
10. The compound
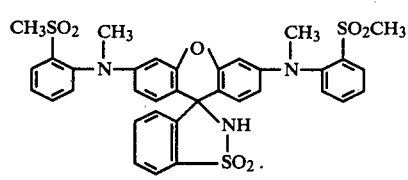
11. The compound
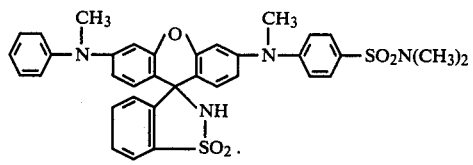
12. The compound
* * * * *